United States Patent
Gundel et al.

(10) Patent No.: US 7,168,292 B2
(45) Date of Patent: Jan. 30, 2007

(54) APPARATUS FOR PARTICULATE MATTER ANALYSIS

(75) Inventors: Lara A. Gundel, Berkeley, CA (US); Michael G. Apte, Berkeley, CA (US); Anthony D. Hansen, Berkeley, CA (US); Douglas R. Black, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 34 days.

(21) Appl. No.: 10/846,103

(22) Filed: May 14, 2004

(65) Prior Publication Data

US 2004/0259267 A1 Dec. 23, 2004

Related U.S. Application Data

(60) Provisional application No. 60/471,478, filed on May 15, 2003.

(51) Int. Cl.
 G01N 37/00 (2006.01)
 G01N 23/00 (2006.01)
 G01N 25/00 (2006.01)
(52) U.S. Cl. .................................... 73/28.01; 73/24.02
(58) Field of Classification Search ............... 73/28.01, 73/28.04, 28.05, 28.06, 24.01, 23.2
See application file for complete search history.

(56) References Cited

U.S. PATENT DOCUMENTS

| 3,458,974 | A | * | 8/1969 | Orr, Jr. et al. ................ 96/221 |
| 3,561,253 | A | | 2/1971 | Dorman |
| 5,268,337 | A | * | 12/1993 | Katz et al. .................... 501/94 |
| 5,892,141 | A | | 4/1999 | Jones et al. |
| 6,413,781 | B1 | | 7/2002 | Geis et al. |
| 6,510,727 | B2 | | 1/2003 | Reiter et al. |
| 6,666,905 | B2 | | 12/2003 | Page et al. |
| 6,923,946 | B2 | * | 8/2005 | Geohegan et al. ....... 423/447.1 |
| 2004/0050207 | A1 | * | 3/2004 | Wooldridge et al. .......... 75/362 |

OTHER PUBLICATIONS

Apte et al, et al., Indoor Measurements of Environmental Tobacco Smoke Final Report to the Tobacco Related Disease Research Program, LBNL 49148, pp. 1-33, A1-59 (Mar. 24, 2004).

* cited by examiner

Primary Examiner—Michael Cygan
(74) Attorney, Agent, or Firm—Fulbright & Jaworski L.L.P.

(57) ABSTRACT

The apparatus described herein is a miniaturized system for particle exposure assessment (MSPEA) for the quantitative measurement and qualitative identification of particulate content in gases. The present invention utilizes a quartz crystal microbalance (QCM) or other mass-sensitive temperature compensated acoustic wave resonator for mass measurement. Detectors and probes and light sources are used in combination for the qualitative determination of particulate matter.

25 Claims, 8 Drawing Sheets

APPARATUS FOR PARTICULATE MATTER ANALYSIS

CROSS REFERENCE TO RELATED APPLICATIONS

This application claims priority to application Ser. No. 60/471,478, filed May 15, 2003, the contents of which are hereby incorporated by reference in their entirety.

STATEMENT AS TO RIGHTS TO INVENTIONS MADE UNDER FEDERALLY SPONSORED RESEARCH OR DEVELOPMENT

The invention described and claimed herein was made in part utilizing funds supplied by the United States Department of Energy under contract No. DE-AC03-76SF000-98 between the United States Department of Energy and The Regents of the University of California. The government has certain rights to the invention.

BACKGROUND OF THE INVENTION

Particulate matter (PM) exposure and health effects have become top US environmental research agenda items over the last decade. Environmental epidemiological studies rely on information from both sides of the dose-response equation: risk factor measures and health outcome data The ability to resolve relationships from environmental data depends upon the quantity, accuracy, specificity and precision of both. Although health surveillance and data collection methods have improved dramatically through database system advances, the techniques for PM exposure are not adequate.

At least three major limitations currently exist for PM measurement. First, PM exposure monitoring is too expensive. Total costs must be reduced by 1–2 orders of magnitude for monitoring within populations to be affordable. Currently, high capital costs make purchasing hundreds of samplers for a single study impractical. Overcoming this obstacle would be extremely beneficial to several types of studies, including measurements of community exposure, exposure variability between individuals in heterogeneous populations, and the relationships among indoor, outdoor, and total personal exposure levels.

Second, PM exposure assessment technology is limited by size, weight, noise, and power constraints. This applies to both area samplers (stationary monitors placed in commonly occupied spaces) and personal samplers (monitors worn by subjects at the breathing zone). The operating noise of area samplers can be very undesirable to study participants. Personal samplers are typically smaller than stationary samplers, but their pumps are usually loud, heavy and bulky. These inconveniences alter subjects' behavior and produce non-representative exposure estimates. Also, the most susceptible populations, children, the elderly, and those with respiratory ailments, often have limited tolerance for such samplers.

Third, simultaneous measurements of several PM characteristics by a single PM device are not typically available. As a result, several types of samplers must be used simultaneously to obtain PM mass, particle size distributions, chemical composition and optical properties. A single 'multi-parameter' sampler that could obtain this range of measurements would be much more practical, especially to identify the sources and mechanisms of health effects.

There is known in the art techniques for measuring PM using resonators, see U.S. Pat. No. 3,561,253. Also, U.S. Pat. No. 5,892,141 uses electrostatic precipitation onto an oscillating surface. U.S. Pat. No. 6,510,727 uses piezoelectric resonators which are provided with at least one collection surface for the particles to be analyzed. Thermoelectric particle precipitators are known in the art, see U.S. Pat. No. 6,666,905. Thermophoretic pumps and concentrators are known in the art, see U.S. Pat. No. 6,413,781 All the aforementioned patents are hereby incorporated herein by reference in their entirety.

A significant benefit of the miniaturized PM samplers in accordance with the present invention is the ability to use them in mail-out surveys where they are deployed in-home, or on-person, by survey participants, reducing the need for trained field personnel. A number of suitable simple miniaturized exposure monitoring devices have been developed for toxic gaseous pollutants, including carbon monoxide, oxides of nitrogen, formaldehyde, volatile organic compounds, and radon.

SUMMARY OF THE INVENTION

The apparatus described herein is a miniaturized system for particle exposure assessment (MSPEA) for the quantitative measurement and qualitative identification of particulate content in gases. The present invention utilizes a quartz crystal microbalance (QCM) or other mass-sensitive temperature compensated acoustic wave resonator for mass measurement. Generally, particles are deposited by thermophoresis onto a piezoelectric resonator surface. The resonator's frequency is monitored. In one embodiment of the present invention there is coupled to the QCM a size selective inlet based on balancing the size-dependent gravimetric settling velocity of particles with the air flow rate through the collector. It is contemplated that the device and method described herein be used in the analysis of emissions from internal combustion engines as well as environmental and industrial pollution monitoring. It is also contemplated that the device described herein may be used in industrial process control and building ventilation control.

DETAILED DESCRIPTION OF THE PREFERED EMBODIMENTS

Figures 1, 2, 3:
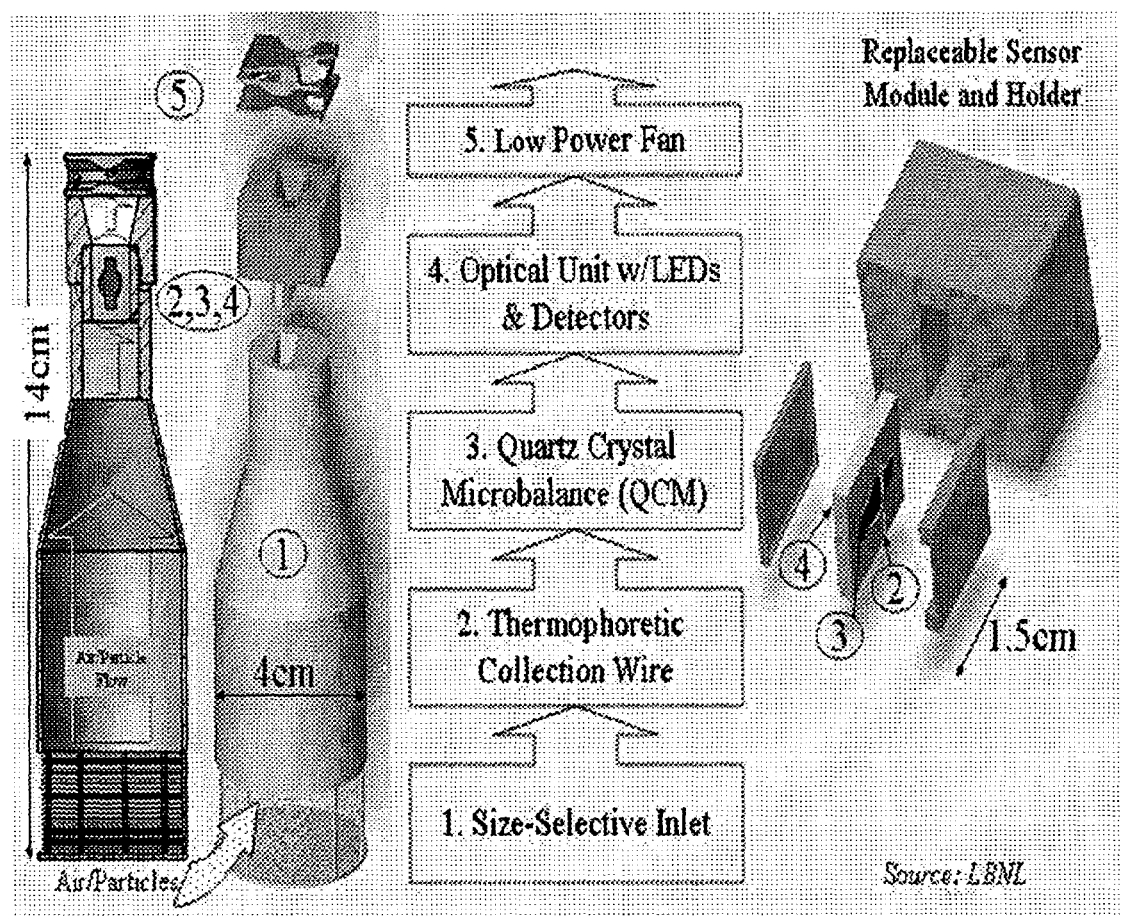
FIG. 1 shows one embodiment of the MSPEA (miniaturized system for particle exposure assessment) construction.
FIG. 2 shows a block diagram of one embodiment of the invention.
FIG. 3 shows a diagram of a replaceable sensor and holder in accordance with one embodiment of the present invention.

In a most preferred embodiment of the present invention the MSPEA comprises four basic elements. However, it is understood that all elements are not necessary for the MSPEA of the present invention to function.

First is an acoustic wave resonator. In a preferred embodiment there is a quartz crystal microbalance (QCM) mass sensor employed as a particulate matter deposition surface. The particulate matter is collected on the surface. The resonator is connected to an electronic oscillator circuit. As particle mass is deposited onto the crystal, mechanical loading reduces the natural resonant frequency of the crystal. The frequency of the sample-collecting crystal is compared to that of a reference crystal to create a difference or "beat" frequency signal. Changes in this difference frequency can be readily determined with an accuracy of 0.1%. The difference frequency changes at a rate (measured in units of hertz per minute) that is proportional to the rate of collection of mass on the crystal surface (measured in units of nanograms per minute). This rate of mass collection is in turn proportional to the mass concentration of particles in the surrounding air. The rate of frequency change can be easily determined by electronic means, to represent a measurement of the mass concentration of particles in the air. These resonators and resonator circuits are known in the art. It is understood that the term "surface" of the resonator may be an electrode of the resonator.

As with all piezoelectric resonators, those used in the MSPEA of the present invention have resonant frequencies that vary with temperature. The resonant frequency of the reference crystal should have the same temperature dependence as the measurement crystal, therefore the beat frequency should be independent of temperature, thus compensating for the inherent temperature dependence of resonating crystals. In some instances, the beat frequency varied with ambient temperature even when both the collection and reference crystals were covered (neither exposed to airborne particles or air movement). This temperature dependence adversely affected the sensitivity of the MSPEA mass sensor. The present invention contemplates using commercially available oscillator/mixing circuit boards to minimize temperature fluctuation induced by the resonator circuitry. In a preferred embodiment, there is an oscillator/mixing circuit coupled to the crystal that will increase the frequency signal to noise ratio, lowering the sensor's detection limit. The oscillator circuit electronics will be well known to those skilled in the art.

QCM's are known in the art, see Applications of Piezoelectric Quartz Crystal Microbalances" in "Methods and Phenomena, Their Applications in Science and Technology", vol. 7, Elsevier 1984; the contents of which are hereby incorporated by reference in its entirety for all purposes. It is understood that the shape of the acoustic wave resonator surface may have any configuration that is known to those skilled in the art and dependent only on engineering design variables. This includes circular, square, etc.

The present invention contemplates that in addition to quartz, other materials may be used as a piezoelectric material. Instead of the quartz crystal microbalance surface the surface material may be Rochelle salts, tourmaline, synthetic crystals such as ethylenediamine tartrate (EDT), dipotassium tartrate (DKT), ammonium dihydrogen phosphate (ATP), ferro electric polymers such as polyvinylidenefluoride (PVDF), polycrystalline ceramic such as lead zirconium titanate ($PbZrTiO_3$), and other crystalline structures such as Zinc Oxide (ZnO), Aluminum Nitride (AlN), Barium Titanate ($BaTiO_3$), Lithium Niobate ($LiNbO_3$) and Lithium Tantalate ($LiTaO_3$).

"Gas" as referred to herein includes air, any industrial or research gas stream, and environmental sample. It is understood that "Gas" as used herein and in the claims also includes mixtures of gases; and said gases may have therein particulate matter of all types and sizes. This includes small masses of liquid and/or solid particles as small agglomerations of molecules including, but not limited to, aerosols, dusts, powders, smokes, mists and fogs, etc.

Second is a thermophoretic particle collector mechanism that precipitates PM from the air onto the resonator surface, where it is usually captured and held, usually by Van der Waal's forces. This employs a "thermophoretic element", which is also termed herein "collection wire", "collector wire", "heating wire", "wire" or "thermophoretic collection device". The particle collector uses the principle of thermophoresis (TP), which is the deposition of particles from the air onto a surface due to a localized temperature gradient. However, it is understood that the present invention contemplates that the thermophoretic element or other THS need only be in proximity to the resonator surface; and by "in proximity" it is meant that during operation of the device at least some of any present particulate matter is deposited on the resonator surface. The invention contemplates that the thermophoretic element or other thermophoretic heated surface (THS) may be above, next to or below the surface. The element may be disposed parallel, or at another non-orthogonal angle to the surface. In one embodiment of the present invention the temperature gradient is produced by a heated thermophoretic element, preferably a wire, a series of wires, or other THS. For example, the thermophoretic element may include a metal strip such as a ribbon, which may have a rectangular shape. The invention also contemplates that a light transmissive metal film or a substrate with a conductive coating be used as the thermophoretic element. The film may be anywhere from 0.1 micron or thicker. The coating may be any thickness desired. For example, there may be an indium tin oxide (ITO) coating on a substrate, such as a glass substrate. This light transmissive metal film may be patterned by techniques known in the art such as lithography. In one embodiment the thermophoretic element may be encased coaxially in an element comprising the resonator, but with an appropriate space between the thermophoretic element and the resonator surface. In one embodiment of the present invention there is used a nickel alloy wire as the thermophoretic element, 25 µm diameter and 15 mm long, stretched parallel to a quartz crystal surface at a distance of 0.5 mm. This configuration will precipitate particles directly from the surrounding ambient atmosphere without the need for pumping the air stream.

Theromophoretic particle collection efficiency increases with increasing temperature gradient between the thermophoretic element and the collection surface. Preferably, the temperature gradient is as high as possible without damaging the device structure or inappropriately altering the particle sample. Measurements made with a 10 µm diameter thermocouple indicated that the temperature difference between the heating wire and the crystal surface was only 5° C. using the sensor configured in FIG. 1. Preferably the temperature gradient is greater than 5° C. In one embodiment of the present invention it is contemplated to decrease the temperature of the resonator by attaching it to a heat sink, preferably a finned aluminum block. However, placing a metal block in contact with some resonator types would dampen its vibration and substantially decrease its sensitivity to deposited mass. Heat can also be transferred via radiation and convection, although not as effectively as with as metal-to-metal conduction. Selection of resonators that can be solidly mounted to a high thermal conductivity surface without hampering their freedom to resonate, but allowing improved heat transfer is possible. The temperature gradient can be increased by cooling the surface of the acoustic wave resonator surface or quartz crystal microbalance surface or heating the thermophoretic element. Means for accomplishing this heating and/or cooling are known in the art.

Third is an optical reflectance system, employing commercial light emitting diodes (LEDs), optical fibers and photodiode detectors, which probes the physical characteristics of collected PM in real time by monitoring the change in resonator surface absorbance of light on the resonator surface. By "light" used herein it is meant light of any wavelength, preferred is UV and NIR. In one embodiment of the present invention there is constructed a MSPEA using an Ocean Optics Inc. (Dunedin, Fla.) reflection/backscattering probe (R200-7Vis) connected to an optic fiber spectrometer (S200) and a tungsten halogen light source (LS-1) mounted to a micro-positioning carriage holding a QCM. The present invention contemplates that this equipment is easily replaced with LED light sources and photodiode light detectors and associated electronics. Quartz optical fibers can be configured above the QCM substrate to pipe the UV and NIR light to the sample substrate and reflected light from the sample substrate to the photodiode detectors. By "probe" it is meant the light detecting element of the apparatus.

The invention contemplates that the optical system is capable of detecting reflected light and transmitted light from the particulate matter of interest. In one embodiment where reflected light is detected, the light source and probe are on the same side of the particulate matter sample. In one embodiment where transmitted light is being detected, the light source and the probe are on the opposite side of the particulate matter sample.

Fourth is a size selective inlet that results in a low-flow system that provides a monitor inlet size cut for PM10 (rejecting 50% of PM mass with aerodynamic diameter>10 µm) or PM 2.5 (rejecting 50% of PM mass with aerodynamic diameter>2.5 µm), based upon size-dependent gravitational settling velocities relative to a vertical inlet sampling velocity. The upper size bound of the aerodynamic diameter size distribution of particles collected by the device can be controlled to match current EPA reference methods inlet cut sizes of PM10 and PM2.5. In one embodiment of the present invention there is contemplated an inlet system for the MSPEA that is generally positioned vertically below the TP collector within a cylindrical tube. However, its relationship to the TP may be on the side or any desired location depending on the specific design chosen as long as the cylindrical tube is positioned vertically. There may be a small fan on one end of a cylindrical tube to induce flow such that sampling linear velocity is lower than the gravitational settling velocity of particles with aerodynamic diameters larger than the desired cut-point size. In operation, terminal gravitational settling velocities ($V_t$) for particles with aerodynamic diameter of 1.0, 5.0 and 10.0 micrometers are 0.036, 0.131 and 0.79 mm sec$^{-1}$, respectively. By adjusting the inlet tube diameter and sampling flow rate, the inlet velocities are controlled such that they are lower than the $V_t$ of the particles of the desired cut-point size. For a 2 cm diameter inlet tube, this translates into sample flow rates of approximately 59 and 4 cm$^3$ min$^{-1}$ for a 10 µm and 2.5 µm size cut, respectively. The size-selective inlet tube may have any shape or diameter, depending on the desired engineering design criteria, however its length should be at least six times that of its radius in order to establish adequate particle size selection prior to collection on the TP collector. In this embodiment, it is important that there be at least a first opening to receive exposure to the environmental gas connected to a second opening that will be connected to a chamber containing the thermophoretic collection wire and mass deposition surface.

In yet another embodiment of the present invention it is contemplated another embodiment of this invention can be assembled where there is no resonator but rather only deposition due to thermophoresis onto a reflective or transmissive surface, which light can be detected with an optical probe either in real time or prior to and post a sampling period. This embodiment will not measure mass directly as it would with a resonator, but it will allow for qualitative discrimination between particle species as with the other embodiments, and will allow for calibrated quantitative estimates of mass of various particle species based on the spectral absorbance measured using the optical probe method discussed in this invention.

FIG. 1 shows one embodiment of the present invention. This figure is illustrative only and not exhaustive of the possible configurations of the present invention. FIG. 1 depicts a substantially tubular MSPEA. Though it is understood the shape is not so limited. The length is only 14 cm long and 4 cm in diameter, which makes it suitable for personal monitoring at a flow of 0.015 L/min and 50% size cut of 2.5 micrometers (PM 2.5). There is disclosed a size-selective inlet (1) attached to a replaceable sensor module and holder that contains the thermophoretic collection wire (2), the quartz crystal microbalance (QCM) and the optical unit with LEDs and detectors (4). Sitting above this is a fan for inducing air flow, in a preferred embodiment. Any flow control module that can provide a consistent and stable flow at the desired flow rate will work for the MSPEA.

FIG. 2 shows a block diagram of the device described in FIG. 1. This consists of a size-selective inlet (1). This inlet device is considered optional in the present invention. A thermophoretic collection wire (2) is essential to the operation of the present invention, as is the quartz crystal microbalance (3). The optical unit w/LEDs and detectors (4) are optional and used for qualitative detection of PM species and source identification. The low power fan (5) is optional if sufficient and stable convective airflow can be established from the heat generated from the thermophoretic source.

FIG. 3 shows a diagram of the replaceable sensor module and holder. The thermophoretic collection wire (2) is shown coupled to the quartz crystal microbalance (3). Shown also is the optical unit (4) for qualitative determinations of PM species and source identification.

In one embodiment of the present invention, a spectrometer was fitted with a light source and a reflectance probe for continuous absorbance measurements of a quartz crystal collection surface. This system was connected to a computer data control and acquisition system and enabled the measurement of the absorbance of light from the ultraviolet to near infrared. The reflectance probe was positioned approximately normal to the quartz crystal surface at a distance of about 3 mm. One of ordinary skill in the art will appreciate that these distances are variable and optimizable depending on the particular configuration of the system. It is preferable that the positioning of the probe relative to the crystal surface be as reproducible as possible. In one embodiment, to ensure reproducible positioning of the probe relative to the crystal surface, a miniature optical bench component was used, FIG. 4. Three parallel collection wires in series can be seen in FIG. 4. Components not shown include the collection resonator which rests on the posts that hold the wire, the quartz slide that is held by the notches below the wire, and the optical reflectance probe which passes through the hole centered beneath the wire.

Figure 4:
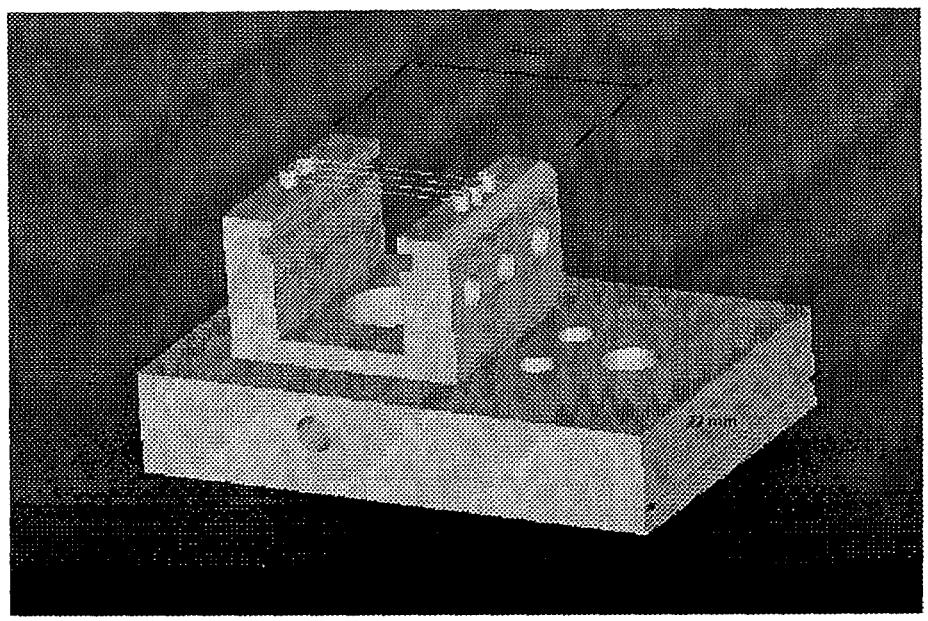
FIG. 4 shows one embodiment where the wire and optical holder form a miniature optical bench upon which a QCM crystal may be mounted.

The FIG. 4 embodiment has three wires to increase collection efficiency, but the invention contemplates that any number of wires or thermophoretic elements, or other appropriate heated source may be used. A quartz slide (with high UV and NIR transmission) was positioned between the heating wire and the face of the optics probe to prevent thermophoretic deposition of particles onto the probe. The slide was used for ease of cleaning compared to the probe surface. The probe was positioned so that its beam of light passed through the slide, past the heating wire, through the collected particle deposit to the reflective chrome surface of the quartz crystal electrode. The reflected light returned the way it came and thus passed twice through the deposited particles, increasing the sensitivity of the optical measurement. The slide was farther from the heating wire than the mass-sensing crystal and, as a result, would collect fewer particles. However, whatever particles were collected on the quartz slide also enhanced the total light absorption.

EXPERIMENTAL

Figure 5:
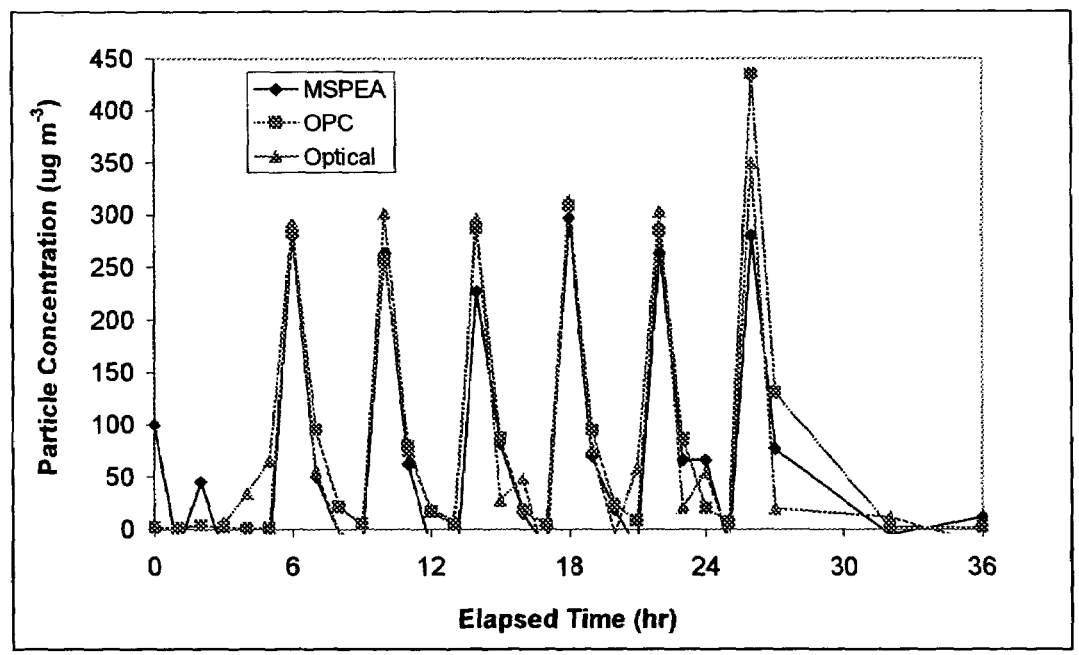
FIG. 5 compares the particulate mass and optical probe blue light (450–480 nm) signal measurement data of the MSPEA with that of a commercial optical particle counter (OPC).

A particle mass concentration analyzer (PMCA, or MSPEA) of the present invention was constructed in accordance with FIG. 4. The PMCA was exposed to environmental tobacco smoke (ETS) in a room-sized test chamber. FIG. 5 compares the particulate mass and optical absorbance (450–480 nm) measurement data of the present invention MSPEA with that of a commercial optical particle counter (OPC), as one cigarette was smoked every four hours for 24 hours in an environmental chamber, and data are averaged for each half hour.

The absorbance changes over each 30 min period were directly proportional to the particle mass concentration measurements made by both an optical particle counter (OPC) and the MSPEA QCM-based mass sensor of the present invention. The two techniques compare well. The optical absorbance, OPC and MSPEA were calibrated using simultaneous measurements made with a ten-stage quartz crystal microbalance cascade impactor.

Figure 6:
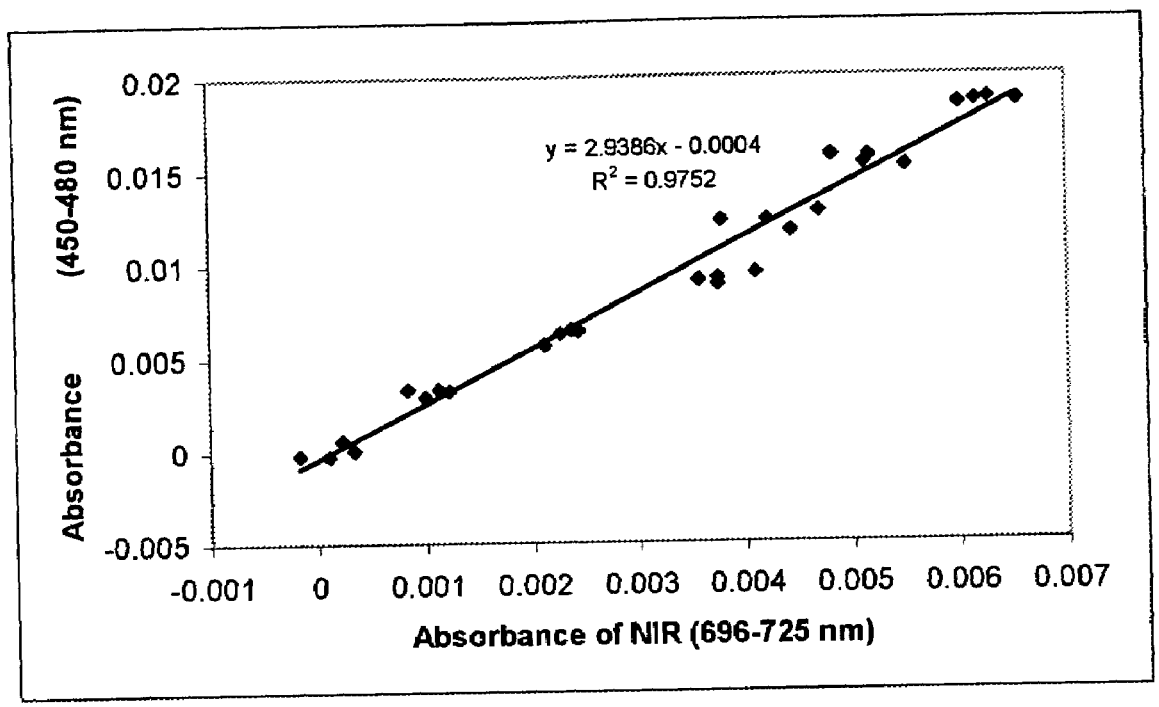
FIG. 6 shows the absorbance of blue light vs. absorbance of NIR light for ETS for the same data as presented in FIG. 5.
Figure 7:
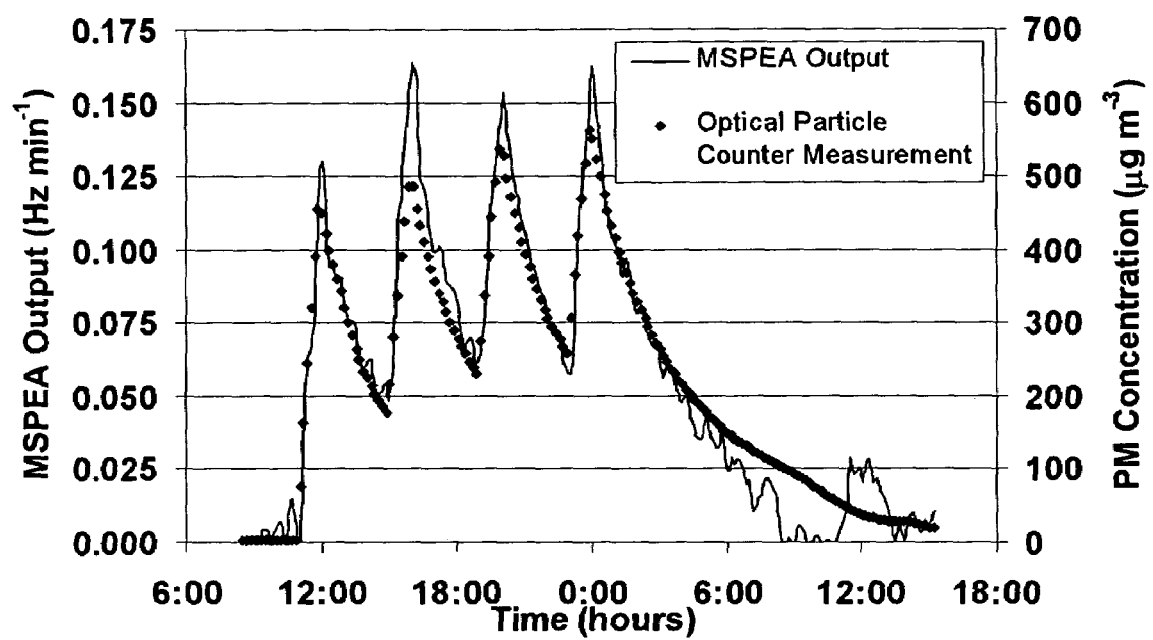
FIG. 7 shows crystal oscillator change in frequency with respect to time and change in response to aerosol (PM) mass collection in real time.
Figure 8:
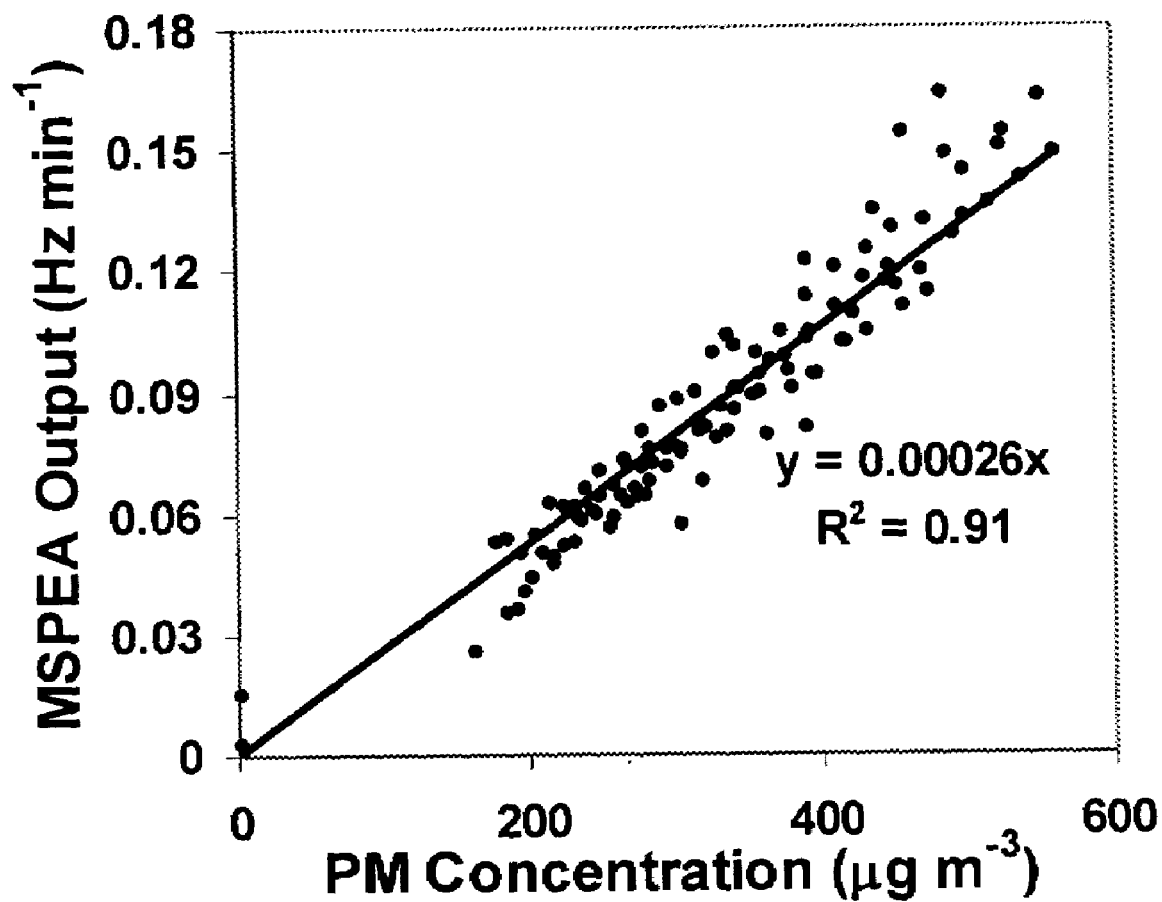
FIG. 8 shows the crystal oscillator response to aerosol (PM) exposure.

Tests were performed with the MSPEA of the present invention constructed in accordance with FIG. 4 with thermal gradients from 2000 to about 5000° K cm$^{-1}$ (wire temperature range: about 100–250° C.; sensor surface temperature generally no more than 3 ° C. higher than ambient). One having ordinary skill in the art will appreciate that due to the volatility of some particulate components it is not desirable to heat the collected particles excessively; however good particle collection was seen in the FIG. 4 configuration with the wire temperature set at 100° C. Chamber experiments with high concentrations of environmental tobacco smoke (ETS) yielded a sharp QCM response, with crystal frequency changes (ΔV) of about 100 Hz indicating collection of about 80 ng of particles on the substrate within a few minutes. Visual inspection of the QCM surface showed a distinct "track" of particle deposition aligned with the wire geometry. Identical tests with the wire unheated yielded no mass changes and no observed deposit. Smoke chamber tests showed that the change in oscillator frequency with respect to time (dF/dt) signal tracked the mass concentration data very well as evidenced in FIG. 6 and FIG. 7. FIG. 6 shows the mass collection on a crystal oscillator and the frequency change in response to aerosol PM. FIG. 8 shows the relationship between the crystal oscillator frequency changes due to thermophoretic particle collection in response to aerosol PM concentration.

The present invention contemplates that the MSPEA may also serve to qualitatively and quantitatively discriminate between particulate matter source contributions. By varying the wavelengths, ETS can be distinguished from diesel-generated particles. FIG. 8 compares the incremental absorbance data (change over 30 min) for two wavelength ranges, blue (450–480 nm) vs the NIR (696–725 nm) for the same experiment as shown in FIG. 5. ETS particles had three times higher absorbance in the blue than in the NIR. The factor is higher when UV and IR are compared. Discrimination between PM components is possible because other PM species respond with different ratios of UV and blue to NIR absorbance. Diesel particles (not shown) have about 1.5 times higher absorbance in the blue than in the NIR. For example, aerosols from biomass combustion have an enhanced UV and blue absorbance with significant NIR absorbance (but less than diesel particles). The MSPEA and related devices can be calibrated using the absorption spectra, based on differences in optical properties of PM sources. For example, using only UV or blue and NIR surface reflectance measurements allows quantification of amounts of PM due to both ETS and diesel particles, after suitable calibration with ETS and diluted diesel particles.

Figure 9:
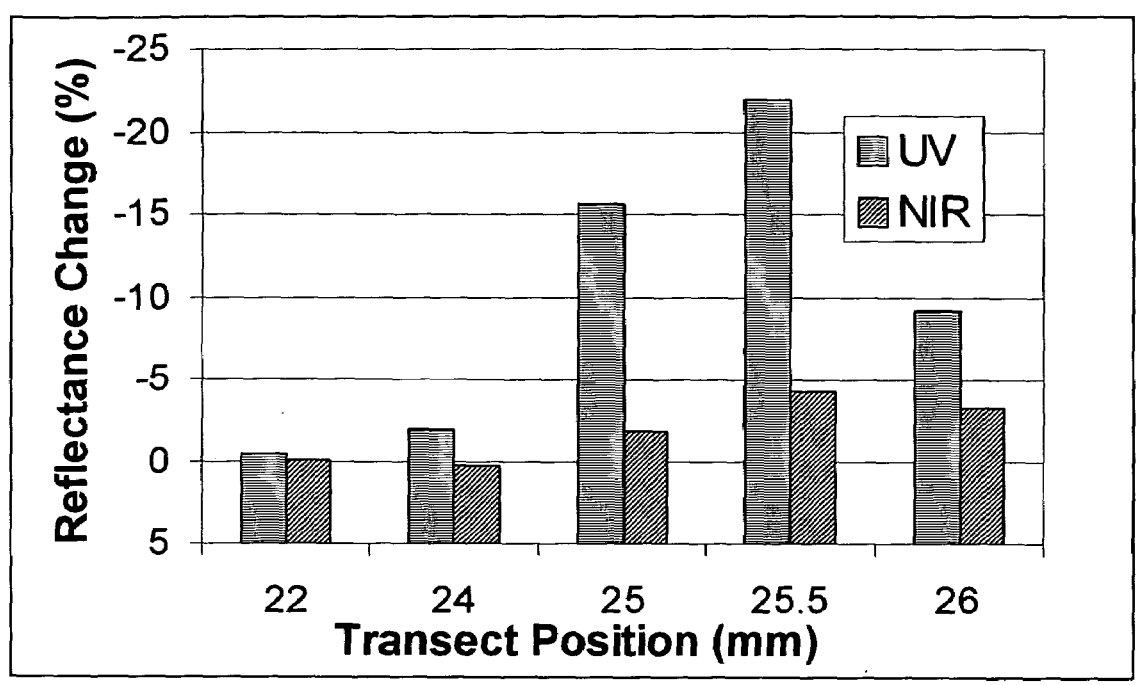
FIG. 9 shows the change in reflectance of the crystal surface UV (375–425 nm) and NIR (750–850 nm) ranges.

To assess the TP deposition pattern qualitative information on PM an Ocean Optics Inc. (Dunedin, Fla.) reflection/backscattering probe (R200-7Vis) was connected to an optic fiber spectrometer (S200) and a tungsten halogen light source (LS-1) was mounted to a micro-positioning carriage holding a lightly loaded (total loading of about 400 ng of ETS) QCM crystal. The probe was positioned normal to and about 2 mm above the surface of the crystal. The results are shown in FIG. 9. FIG. 9 shows the change in reflectance of the crystal surface (relative to a clean crystal) in the UV (375–425 nm) and NIR (750–850 nm) ranges, for a transect across the crystal surface, orthogonal to the TP wire axis. The reflection was strongly attenuated in the UV region due to the characteristic UV absorbing properties of the ETS, while the NIR reflectance was only slightly attenuated. The TP deposition pattern is verified for this system configuration.

Figure 10:
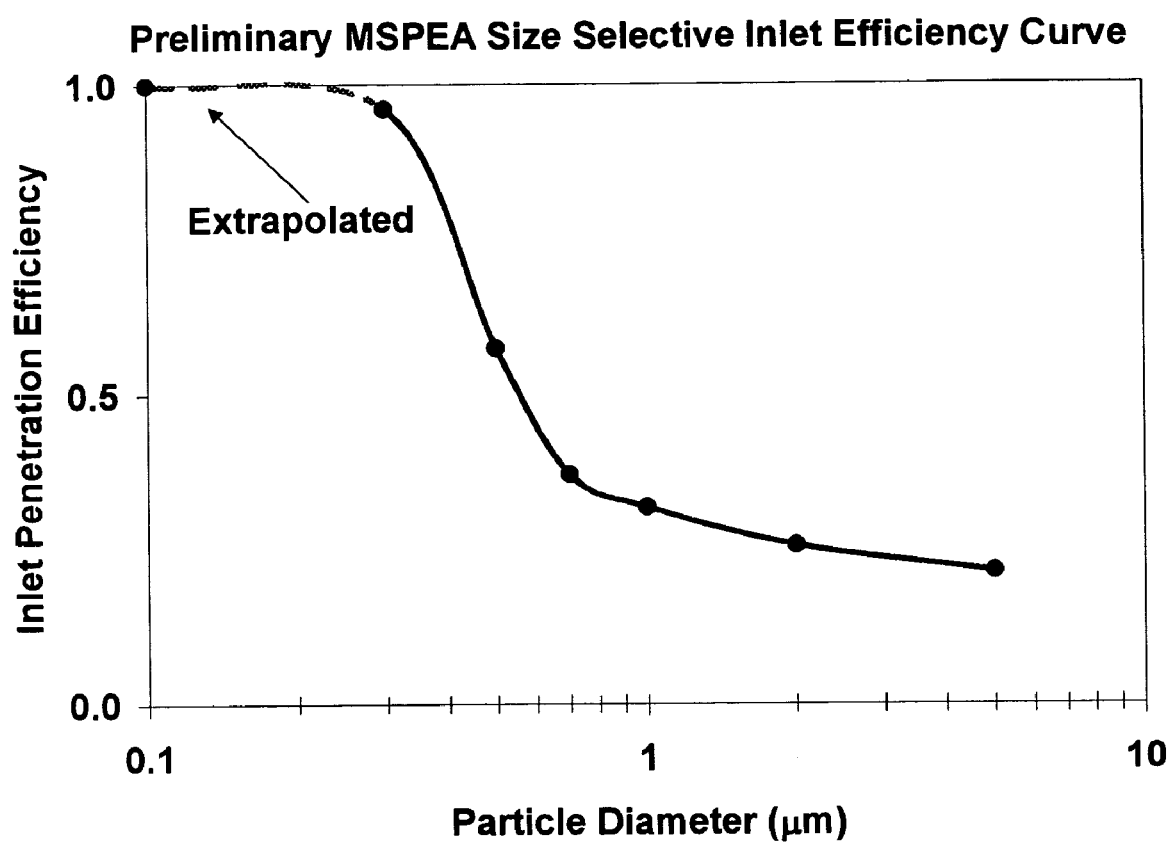
FIG. 10 shows the particle size penetration into a 25 cm diameter vertical tube with a sampling rate of 2.83 liter/min.

Experiments were conducted in order to demonstrate the use of the gravitational particle size separator. FIG. 10 shows the particle size penetration into a 25 cm diameter vertical tube with a sampling rate of 2.83 liter/min. FIG. 10 shows a size selective inlet with cut size of 0.5 micrometer particle diameter. The ratio of inlet diameter and sampling rate controls the cut point. Therefore this design can be scaled up or down and achieve the same cut point for different flow rates. One of ordinary skill in the art will recognize the engineering parameters necessary to scale this up or down to achieve the desired cut point for different flow rates.

Figure 11:
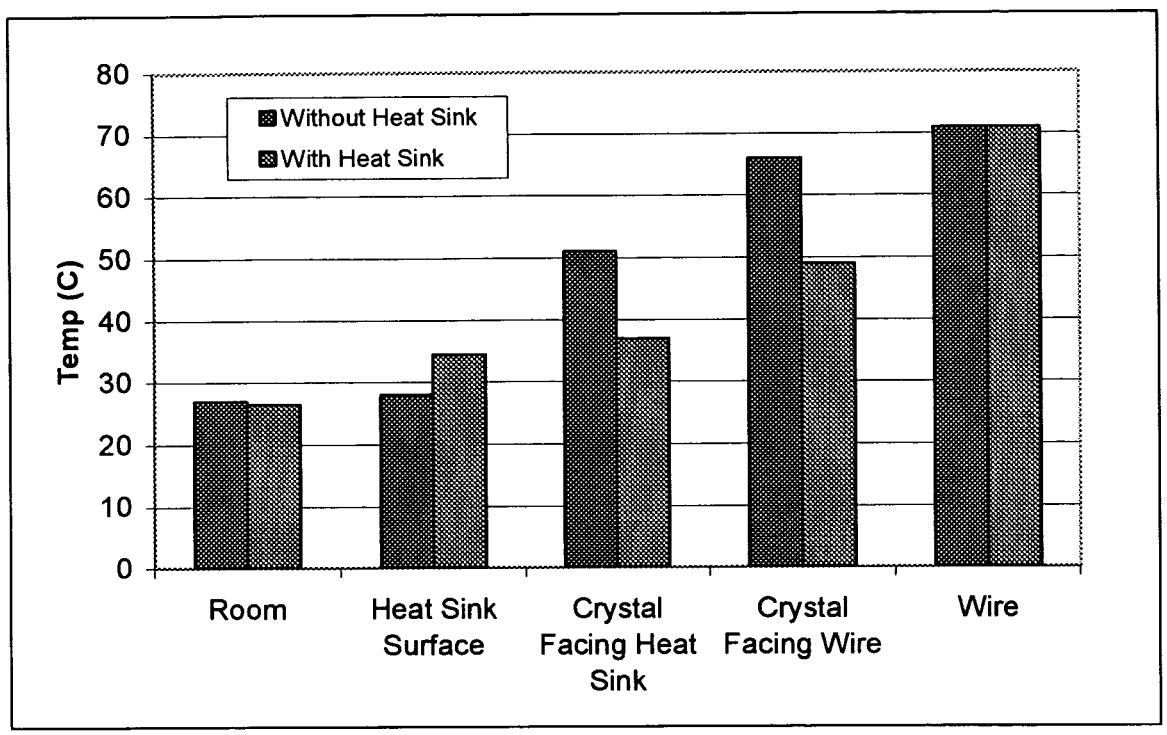
FIG. 11 shows the temperature of various sensor components with and without a heat sink placed within 1 mm of the collection crystal.

A MSPEA was constructed in accordance with FIG. 4. When a black anodized, finned aluminum heat sink was placed within 1 mm of the crystal surface, opposite the surface facing the wire, the temperature gradient between the wire and the crystal increased from 5° C. to 22° C., as shown in FIG. 11. FIG. 11 also shows the temperatures of various sensor components with and without a heat sink placed within 1 mm of the collection crystal.

Enhanced thermal gradients can be created by improving the thermal conduction from the resonator surface by mounting it onto a finned heat sink or other cooling device such as a thermoelectric cooler. Shear wave resonators such as the ST-cut quartz crystal cannot be directly mounted onto a solid surface, except at their perimeter, without significant dampening of their ability to resonate. Other available resonator designs that will be appreciated by those familiar with the art can be solidly mounted to a thermally conductive surface without significant dampening of their ability to freely resonate.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention.

All patents, patent applications, and publications mentioned above are herein incorporated by reference in their entirety for all purposes. None of the patents, patent applications, and publications mentioned above are admitted to be prior art.

What is claimed is:

1. An apparatus for the analysis of particulate content of a gas comprising:
    at least one thermophoretic element comprising a light transmissive metal film,
    at least one acoustic wave resonator having a surface, and
    an electronic oscillator circuit connected to the acoustic wave resonator, wherein:
    the at least one thermophoretic element is positioned in proximity to the at least one surface of the acoustic wave resonator to deposit the particulate content of the gas on the surface of the acoustic wave resonator.

2. The apparatus for the analysis of particulate content of a gas as claimed in claim 1, further comprising:
    at least one source of light capable of illuminating at least some of any present particulate matter in the apparatus, and
    at least one probe, wherein:
    the at least probe is capable of detecting light transmitted through the at least some of any present particulate matter in the apparatus.

3. The apparatus for the analysis of particulate content of a gas as claimed in claim 1, wherein:
    there are between 2 and 1,000 thermophoretic elements.

4. The apparatus for the analysis of particulate content of a gas as claimed in claim 1, wherein:
    the thermophoretic element is positioned from the acoustic wave resonator surface at a distance of from between 0.1 and 10 mm.

5. The apparatus for the analysis of particulate content of a gas as claimed in claim 1, wherein:
    there is a temperature gradient between the thermophoretic article and the acoustic wave resonator surface of between 0.5° C. and 400° C.

6. The apparatus for the analysis of particulate content of a gas as claimed in claim 1, further comprising:
    at least one heat sink coupled to the acoustic wave resonator.

7. The apparatus for the analysis of particulate content of a gas as claimed in claim 1, further comprising:
    a size selective inlet comprising a chamber having at least a first opening and a second opening, said size selective inlet capable of controlling the size of particulate matter flowing through the apparatus.

8. The apparatus for the analysis of particulate content of a gas as claimed in claim 7, wherein:
    the first opening is exposed to the environment such that a gas is capable of entry into the first opening, and
    the second opening is connected to a unit containing the thermophoretic element and acoustic wave resonator, and
    a fan disposed on the apparatus in a position such that a gas may be drawn through the first opening and into the unit containing the thermophoretic element and acoustic wave resonator.

9. The apparatus for the analysis of particulate content of a gas as claimed in claim 1, further comprising:
    at least one source of light capable of illuminating at least some of any present particulate matter in the apparatus, and
    at least one probe, wherein:
    the at least one probe is capable of detecting light reflected from the at least some of any present particulate matter in the apparatus.

10. The apparatus for the analysis of particulate content of a gas as claimed in claim 9, further comprising:
    a spectrophotometer, a photodetector or photodetector ray connected to the at least one probe.

11. The apparatus for the analysis of particulate content of a gas as claimed in claim 1, wherein:
    the thermophoretic element further comprises at least one wire.

12. The apparatus for the analysis of particulate content of a gas as claimed in claim 1, wherein:
    there is a temperature gradient between the at least one acoustic wave resonator and the at least one thermophoretic element.

13. The apparatus forte analysis of particulate content of a gas as claimed in claim 1, wherein:
    the at least one acoustic wave resonator is disposed inside a tubular shaped structure.

14. The apparatus for the analysis of particulate content of a gas as claimed in claim 1, wherein:
    the light transmissive metal film is patterned.

15. The apparatus for the analysis of particulate content of a gas as claimed in claim 1, wherein:
    the acoustic wave resonator is a quartz crystal microbalance.

16. The apparatus for the analysis of particulate content of a gas as claimed in claim 1, wherein:
    the acoustic wave resonator comprises a material selected from the group consisting of quartz, Rochelle salts, tourmaline, ethylenediamine tartrate (EDT), dipotassiuan tartrate (DKT), ammonium dihydrogen phosphate (ATP), ferroelectric polymers, polycrystalline ceramics, Zinc Oxide (ZnO), Aluminum Nitride (AlN), Barium Titanate ($BaTiO_3$), Lithium Niobate ($LiNbO_3$) and Lithium Tantalate ($LiTaO_3$).

17. An apparatus for the analysis of particulate content of a gas comprising:

at least one thermophoretic element, at least one acoustic wave resonator having a surface, wherein the at least one thermophoretic element is positioned in proximity to the at least one surface of the acoustic wave resonator to deposit the particulate content of the gas on the surface of the acoustic wave resonator, at least one source of light capable of illuminating at least some of any present particulate matter in the apparatus, and at least one probe, wherein the at least one probe is capable of detecting light reflected from the at least some of any present particulate matter in the apparatus; and wherein the at least one probe comprises a plurality of probes.

18. The apparatus for the analysis of particulate content of a gas as claimed in claim 17, wherein:

the plurality of probes comprise quartz optical fibers, and are disposed above the acoustic wave resonator.

19. An apparatus for the analysis of particulate content of a gas comprising:

at least one thermophoretic element, and at least one collection surface, wherein:

the at least one thermophoretic element is positioned in proximity to the at least one collection surface, wherein the at least one collection surface is capable of reflecting light or transmitting light.

20. An apparatus for the analysis of particulate content of a gas as claimed in claim 19, wherein:

the at least one collection surface is capable of reflecting light.

21. An apparatus for the analysis of particulate content of a gas as claimed in claim 19, wherein:

the at least one collection surface is capable of transmitting light.

22. An apparatus for the analysis of particulate content of a gas comprising:

at least one thermophoretic element, at least one acoustic wave resonator having a surface, wherein the at least one thermophoretic element is positioned in proximity to the at least one surface of the acoustic wave resonator;

at least one source of light capable of illuminating at least some of any present particulate matter in the apparatus, at least one probe, wherein said at least one probe is capable of detecting light reflected from the at least some of any present particulate matter in the apparatus; and a spectrophotometer, a photodetector or photodetector array connected to the at least one probe, wherein the at least one probe comprises a plurality of probes.

23. The apparatus for the analysis of particulate content of a gas as claimed in claim 22, wherein the plurality of probes comprise quartz optical fibers, and are disposed above the acoustic wave resonator.

24. An apparatus for the analysis of particulate content of a gas comprising:

at least one thermophoretic element comprising a light transmissive metal film, and at least one acoustic wave resonator having a surface, wherein the at least one thermophoretic element is positioned in proximity to the at least one surface of the acoustic wave resonator.

25. The apparatus forte analysis of particulate content of a gas as claimed in claim 24, wherein the light transmissive metal film is patterned.

* * * * *